(12) United States Patent
Sanjayan et al.

(10) Patent No.: US 10,385,096 B2
(45) Date of Patent: Aug. 20, 2019

(54) PRO-AMB REVERSE TURN RESTRICTED BIOACTIVE PEPTIDE ANALOGUES

(71) Applicant: Council of Scientific & Industrial Research, New Delhi (IN)

(72) Inventors: Gangadhar J. Sanjayan, Pune (IN); Ganesh S. Jedhe, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/360,698

(22) Filed: Nov. 23, 2016

(65) Prior Publication Data
US 2018/0057529 A1    Mar. 1, 2018

(30) Foreign Application Priority Data

Aug. 30, 2016 (IN) .............................. 201611029463

(51) Int. Cl.
   *C07K 5/02*     (2006.01)
   *C07K 7/14*     (2006.01)
   *A61K 38/00*    (2006.01)
(52) U.S. Cl.
   CPC .............. *C07K 5/0202* (2013.01); *C07K 7/14* (2013.01); *A61K 38/00* (2013.01)
(58) Field of Classification Search
   None
   See application file for complete search history.

(56) References Cited

U.S. PATENT DOCUMENTS

| 7,741,357 B1* | 6/2010 | Huang ............... C07C 69/96 514/231.2 |
| 8,133,877 B2* | 3/2012 | Al-Mahmood ...... A61K 31/713 435/375 |
| 2010/0297132 A1* | 11/2010 | Greferath ........... A61K 39/3955 424/139.1 |
| 2012/0157513 A1* | 6/2012 | Li ........................ C07K 7/14 514/44 R |
| 2014/0378410 A1* | 12/2014 | Baik ................... A61K 31/655 514/54 |
| 2016/0347794 A1* | 12/2016 | Hay ...................... C07K 7/06 |

OTHER PUBLICATIONS

Berretta "Sonic hedgehog stimulates neurite outgrowth in a mechanical stretch model of reactive-astrogliosis" scientific reports 6:21896 (Year: 2016).*
Takane "Detrimental Effects of Centrally Administered Angiotensin II are Enhanced in a Mouse Model of Alzheimer Disease Independently of Blood Pressure" J Am Heart Assoc 6:e004897 (Year: 2017).*
Kim "Angiotensin II Causes Apoptosis of Adult Hippocampal Neural Stem Cells and Memory Impairment Through the Action on AMPK-PGC1a Signaling in Heart Failure" stem cell trans med 6:1491-1503 (Year: 2017).*

(Continued)

*Primary Examiner* — Adam Weidner
(74) *Attorney, Agent, or Firm* — Locke Lord LLP; Nicholas J. DiCeglie, Jr.

(57) ABSTRACT

The present invention discloses novel peptides acting as angiotensin II analog for therapeutic applications. Said peptides can be used for treatment of Alzheimer's and other neurological and cognitive disorders.

7 Claims, 9 Drawing Sheets

Specification includes a Sequence Listing.

(56) References Cited

OTHER PUBLICATIONS

Nade "cognitive enhancing effect of angiotensin-converting enzyme inhibitors and angiotensin receptor blockers on learning and memory" indian j pharma 47(3):263-269 (Year: 2015).*

U. Rosenstrom et al., "A Selective $AT_2$ Receptor Ligand with a γ-Turn-Like Mimetic Replacing the Amino Acid Residues 4-5 of Angiotension II," J. Med. Chem 47, 859-870, (2004).

P. K. Baruah et al., "Enforcing Periodic Secondary Structures in Hybrid Peptides: A Novel Hybrid Foldamer Containing Periodic γ-Turn Motifs," J. Org. Chem 72, 636-639, (2007).

E. J. Milner-White et al., "One Type of Gamma-turn, Rather Than the Other Gives Rise to Chain-reversal in Proteins," J. Mol. Biol. 204, 777-782, (1988).

E. J. Milner-White, "Situations of Gamma-turns in Proteins—Their Relation to Alpha-helices, Beta-sheets and Ligand Binding Sites," J. Mol. Biol. 216, 385-397, (1990).

I. Alkorta et al., "Similarity Study on Peptide γ-turn Conformation Mimetics," J. Mol. Model 2, 16-25, (1996).

\* cited by examiner

SEQUENCE LISTING

```
<160> NUMBER OF SEQ ID NOS: 4

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
```

```
<223> OTHER INFORMATION: 3-amino-2-methoxybenzoic acid

<400> SEQUENCE: 1

Asp Arg Pro Xaa Ile His Pro Phe
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: 3-amino-2-methoxybenzoic acid

<400> SEQUENCE: 2

Asp Arg Pro Xaa Ile His Pro
1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 3-amino-2-methoxybenzoic acid

<400> SEQUENCE: 3

Arg Pro Xaa Ile
1

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Arg Val Tyr Ile His Pro Phe
1               5
```

PRO-AMB REVERSE TURN RESTRICTED BIOACTIVE PEPTIDE ANALOGUES

CROSS REFERENCE TO RELATED APPLICATIONS

This application claims the benefit of priority of Indian Patent Application No. IN 201611029463, fled Aug. 30, 2016. The contents of which are hereby incorporated herein by reference in their entirety.

SEQUENCE LISTING

The instant application contains a Sequence Listing which has been submitted electronically in ASCII format and is hereby incorporated by reference in its entirety. Said ASCII copy, created on Nov. 22, 2016, is named 1451121_144US2_SL.txt and is 1,367 bytes in size.

TECHNICAL FIELD OF THE INVENTION

The present invention relates to a novel peptide analogue for therapeutic applications. More particularly, the present invention relates to an angiotensin II analogue for therapeutic use in treatment of Alzheimer's and other neurodegenerative diseases.

BACKGROUND AND PRIOR ART OF THE INVENTION

The secondary structure of a protein is characterized by regular elements such as alpha (α) helices, beta (β) sheets and irregular elements such as β bulges, tight turns and random coils. Tight turns are one of the three "classical" secondary structures with approximately one-third of all residues in globular proteins comprised in turns that serve to reverse the direction of polypeptide chain. Gamma turns is the second most characterized and commonly found tight turn in proteins after β-turns. γ-turn comprise of 3.4% of amino acids and are defined as 3 residue turns with H-bond between the carbonyl oxygen of residue (i) and the hydrogen of the amide group of residue (i+2). Search and analysis of 54 proteins by Miner-White, E J, et. al. (J. Mol. Bio. 204, 1983, pp. 777-82) indicated nine proteins to have eleven classic γ-turns, and these eleven turns had mean φ and ψ values at residue i+1 of +75.0 and −64, respectively. Seven of these eleven turns are involved in formation of β-hairpins which produce a reversal in the peptide chain.

Gamma turns are present at ligand binding sites or active sites. It has further been postulated by Milner-White, E J, et. al. (J. Mol. Biol. 204, 1990, pp. 385-397) that inverse gamma turns may function as intermediates in folding and thus stabilizing β-strands before they become β-sheets. Recently, gamma-turns have attracted attention through studies that describe incorporation of peptide secondary structure mimetics into small bioactive peptides in development of stable, effective and selective receptor ligands Alkorta, I, et al. (J. Mol. Model, 2, 1996, pp. 16-25). Proteins having a turn like conformation include angiotensin, thermolysin, tobacco necrosis virus protein, flavodoxin, proteinase A, α-lytic protease and other small cyclic peptides.

Angiotensin II (Ang II) is an important peptide regulating cardiovascular hemodynamics and cardiovascular structure. Most of the known effects of Ang II in adult tissues are attributable to the angiotensin II type I ($AT_1$) receptor although it is well known to bind both the $AT_1$ and $AT_2$ receptor. The $AT_1$ and $AT_2$ receptors have differential pharmacological and biochemical properties and appear to exert opposite effects in terms of cardiovascular hemodynamics and cell growth. In addition, the renin-angiotensin and nitric oxide-generating systems appear to interact in the regulation of cardiovascular function. Ang II stimulates angiogenesis and increases micro-vessel density. In nature, angiotensin II is produced by the action of angiotensin converting enzyme on angiotensinogen; the C-terminal-His-Leu is cleaved.

Angiotensin II (Ang II), an octapeptide having sequence, i.e. Asp-Arg-Val-Tyr-Ile-His-Pro-Phe (SEQ ID NO: 4), is an endogenous substrate for $AT_1$ and $AT_2$ receptors. Ang II adopts a turn-like conformation centered at $Val^3$-$Tyr^4$-$Ile^5$ residue while interacting with the angiotensin receptors.

A reverse turn like conformation in angiotensin II has been mimicked by incorporation of thio-linkage, benzodiazepine-derivative, 3-aminobenzoicacid, etc. with enhanced affinity for $AT_2$ receptors. Hallberg et al (J. Med. Chem., 2004, 47 (4), pp 859-70) have disclosed the design and synthesis of three angiotensin II analogues comprising a benzodiazepine-based γ-turn-like scaffold. However, introduction of such chemically synthesized compounds or their derivatives in a peptide sequence of angiotensin II may cause a change in the configuration of the protein and consequently affect the binding ability of the protein. Further issues relating to the cytotoxicity and delivery of the analogues may also arise.

There is a large body of documented work relating to design and synthesis of peptide analogues of peptides such as angiotensin II synthesized by incorporation of chemically synthesized moieties to confer a mimetic gamma turn in the bioactive peptide. However, none of the prior arts suggest or teach incorporation of a peptide based hydrogen bonding directing reverse-turn scaffold.

The present inventors have earlier synthesized a gamma turn mimetic foldamer in tripeptides and tetra-peptides (P. K. Baruah, et al, J. Org. Chem., 2007, 72, 636). The foldamer comprises proline and 3-amino-5-bromo-2-methoxy benzoic acid as alternating subunits that forms repeating γ-turn conformations. However, the γ-turn conformation was demonstrated in only non-polar organic solvent chloroform and their applications were not demonstrated. None of the prior art provides the conformational studies under aqueous solutions essential for physiological functions.

Several therapeutic peptides and peptide analogues designed do not have ideal pharmacokinetics, bioavailability and toxicity profiles. Therefore, chemically synthesized analogues of angiotensin II and other such bioactive peptides have not been used to their complete potential as a therapeutic agent for treatment of neurological or other disorders. Therefore, there is a need in the art to provide a peptide analogue comprising incorporation of peptide-based hydrogen bonding directing reverse-turn scaffold stable under aqueous conditions in a peptide sequence having better bioavailability, low cytotoxicity and better pharmacokinetic profiles.

OBJECTIVE OF THE INVENTION

An objective of the present invention is to provide a novel peptide analogue comprising peptide-based hydrogen bonding directing reverse-turn scaffold for therapeutic applications.

Another object of the present invention is to provide a novel peptide analogue for treatment of neurodegenerative disorders such as Alzheimer's disease and other diseases associated with neuronal functions.

SUMMARY OF THE INVENTION

In an aspect, the present invention provides a peptide or a fragment thereof having the formula I:

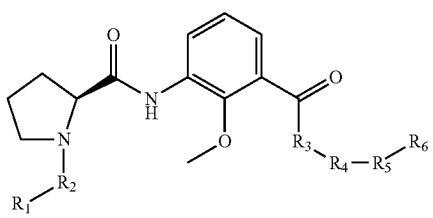

Formula I wherein $R_1$ is selected from the group consisting of aspartate (Asp), tyrosine (Tyr) and alanine (Ala), or $R_1$ is absent;

$R_2$ is selected from the group consisting of serine (Ser), arginine (Arg) and isoleucine (Ile);

$R_3$ is selected from the group consisting of tyrosine (Tyr), isoleucine (Ile) and serine (Ser);

$R_4$ is selected from the group consisting of tyrosine (Tyr), histidine (His) and glutamate (Glu), or $R_4$ is absent;

$R_5$ is selected from the group consisting of leucine (Leu), proline (Pro) and threonine (Thr), or $R_5$ is absent;

$R_6$ is selected from the group consisting of glutamate (Glu) and phenylalanine (Phe), or $R_6$ is absent;

wherein proline-3-amino-2-methoxy benzoic acid (Pro-Amb) as a γ turn is incorporated between $R_2$ and $R_3$.

Another aspect of the present invention provides the sequence of peptide having formula I selected from the group consisting of SEQ ID NO: 1 (Asp-Arg-Pro-Xaa-Ile-His-Pro-Phe), SEQ ID NO: 2 (Asp-Arg-Pro-Xaa-Ile-His-Pro) and SEQ ID NO: 3 (Arg-Pro-Xaa-Ile), wherein "Xaa" represents 3-amino-2-methoxybenzoic acid, a non-coded amino acid abbreviated as Amb.

Still another aspect of the present invention provides a peptide or a fragment thereof having sequence selected from the group consisting of SEQ ID NO: 1, SEQ ID NO: 2 and SEQ ID NO: 3, wherein the peptide or a fragment thereof is an analogue of angiotensin II.

Another aspect of the present invention provides a composition comprising the peptide having formula I for inducing neurite outgrowth in neuronal cells.

Yet another aspect of the present invention provides a method of administration of a composition comprising the peptide having formula I in an individual diagnosed with a cognitive disease or a neurological disease or showing symptoms of said cognitive disease or neurological disease.

Still another aspect of the present invention provides a method for treating a subject with a cognitive or a neurological disease comprising administering a therapeutically effective amount of a peptide or fragments thereof having Formula I or mixture thereof to a subject diagnosed with said cognitive or neurological disease or to a subject exhibiting symptoms of said disease followed by administering an Angiotensin II receptor ($AT_2R$) agonist either simultaneously with the peptide or after a time interval.

DETAILED DESCRIPTION OF DRAWINGS

DETAILED DESCRIPTION OF THE INVENTION

Figure 1A:
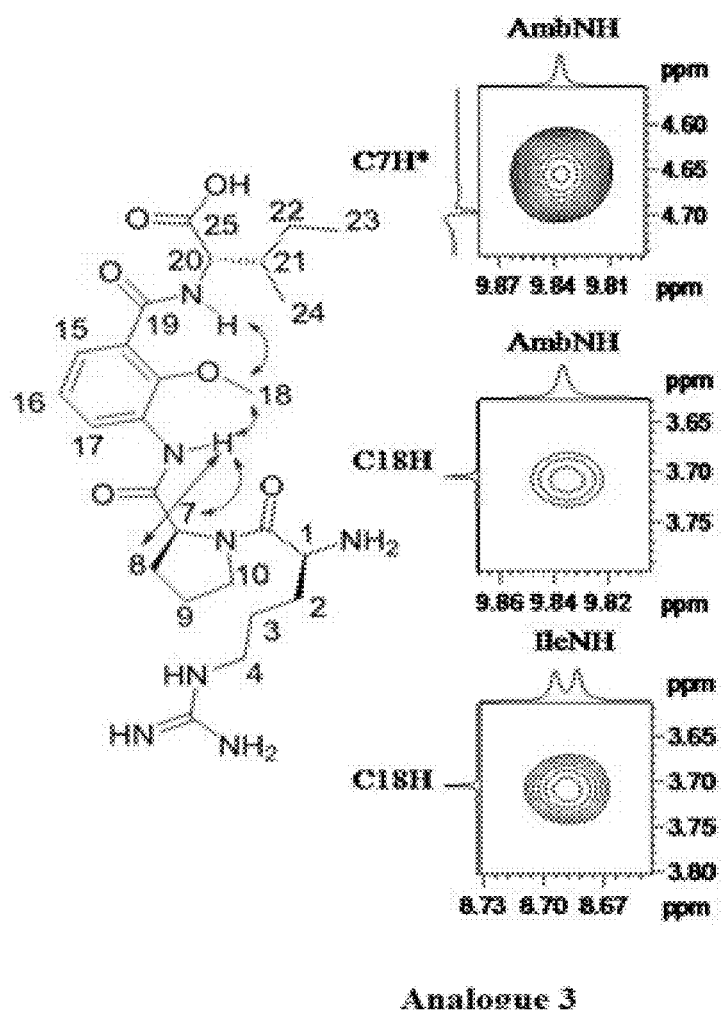
FIG. 1(a) represents the chemical structure and characteristic ROE excerpts for γ-turn conformation [$H_2O:D_2O$, (9:1), 700 MHz, 298K] of Arg-Pro-Amb-Ile (Analogue 3) (SEQ ID NO: 3). *The C7H proton signals were not distinctly visible due to water suppression.

The invention will now be described in detail in connection with certain preferred and optional embodiments, so that various aspects thereof may be more fully understood and appreciated.

For the purposes of the present invention, the designations SEQ ID NO: 1, 2 and 3 can be interchangeably used with analogue 1, analogue 2, and analogue 3, respectively.

An embodiment of the present invention provides a peptide or a fragment thereof having the formula I:

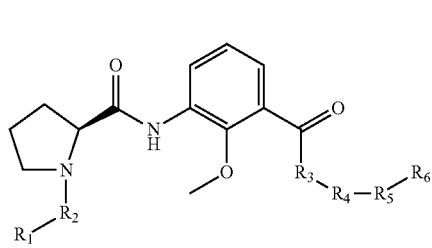

Formula I wherein $R_1$ is selected from the group consisting of aspartate (Asp), tyrosine (Tyr) and alanine (Ala), or $R_1$ is absent;

$R_2$ is selected from the group consisting of serine (Ser), arginine (Arg) and isoleucine (Ile);

$R_3$ is selected from the group consisting of tyrosine (Tyr), isoleucine (Ile) and serine (Ser);

$R_4$ is selected from the group consisting of tyrosine (Tyr), histidine (His) and glutamate (Glu), or $R_4$ is absent;

$R_5$ is selected from the group consisting of leucine (Leu), proline (Pro) and threonine (Thr), or $R_5$ is absent;

$R_6$ is selected from the group consisting of glutamate (Glu) and phenylalanine (Phe), or $R_6$ is absent, wherein proline-3-amino-2-methoxy benzoic acid scaffold (Pro-Amb) as a γ turn is incorporated between $R_2$ and $R_3$.

Another embodiment of the present invention provides the sequence of peptide having formula I selected from the group consisting of SEQ ID NO: 1 (Asp-Arg-Pro-Xaa-Ile-His-Pro-Phe), SEQ ID NO: 2 (Asp-Arg-Pro-Xaa-Ile-His-Pro) and SEQ ID NO: 3 (Arg-Pro-Xaa-Ile), wherein "Xaa" represents 3-amino-2-methoxybenzoic acid, a non-coded amino acid abbreviated as Amb.

Still another embodiment of the present invention provides a peptide or a fragment thereof having sequence selected from the group consisting of SEQ ID NO: 1, SEQ ID NO: 2 and SEQ ID NO: 3, wherein the peptide or a fragment thereof is an analogue of angiotensin II.

For the purpose of the present invention, "Xaa" has been replaced with "Amb" in the sequence of analogue 1, analogue 2 and analogue 3 in the description and figures.

Angiotensin II is an octapeptide hormone that plays a central role in cardiovascular homeostasis and its native sequence is $Asp^1$-$Arg^2$-$Val^3$-$Tyr^4$-$Ile^5$-$His^6$-$Pro^7$-$Phe^8$ (SEQ ID NO: 4).

Analogue 1 is designed by replacement of $Val^3$-$Tyr^4$ residue of the native sequence of angiotensin II (Ang II) with Pro-Amb scaffold. Similarly, analogue 2 is designed by replacement of $Val^3$-$Tyr^4$ residues of Ang II by Pro-Amb scaffold and removal of $Phe^8$. Analogue 3 comprises minimum amino acids wherein the Pro-Amb scaffold is introduced by merely extending one residue on N-terminus as well as C-terminus.

Water clusters are dynamic in nature and hence, mimicking and characterization of peptidic secondary structure in aqueous solution can be challenging. Therefore, peptidic reverse turn scaffold, i.e. the Pro-Amb scaffold developed from unnatural amino acids with distinct secondary structure in an aqueous solution has wide applications in development of potential therapeutic agents.

The choice of NMR solvent was decided mainly due to water solubility of the modified peptides and bio-activity testing in aqueous solution. Extensive solution-state NMR studies were carried out in $H_2O:D_2O$ (9:1). The complete assignments of NMR spectra were done using COSY, TOCSY, HMBC and HSQC. Further, the ROESY spectrum of analogue 3 was examined for signatures of anticipated γ-turn between proline and Amb residues. The Nuclear Overhauser Effect (NOE) between Amb-NH and α-hydrogen of proline (C7H) confirms γ-turn formed between AmbNH and carbonyl group of arginine [FIG. 1(a)]. The NOE observed between AmbNH and β hydrogens (C18H) of the proline further supports this γ-turn conformation. The methyl from methoxy group of Amb showed NOE interactions with Amb NH and IleuNH—confirming extended 5- and 6-membered hydrogen bonds, respectively [FIG. 1(a)].

Figure 1B:
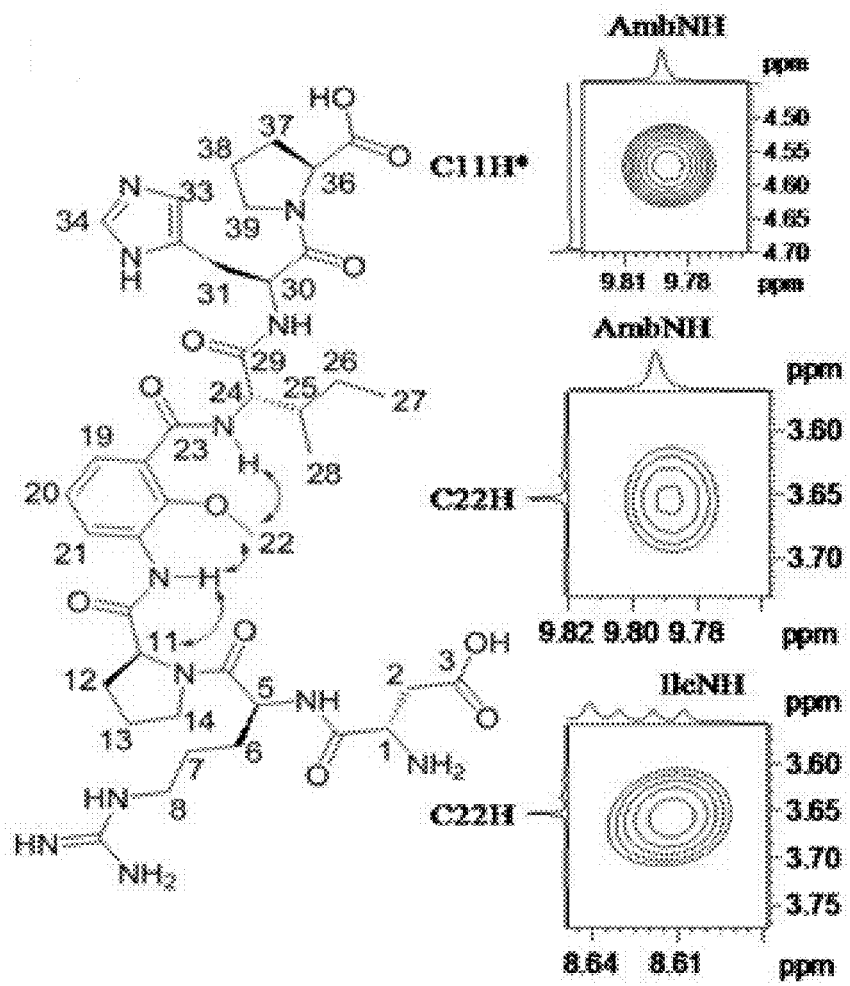
FIG. 1(b) represents the chemical structure and characteristic ROE excerpts for γ-turn conformation [$H_2O:D_2O$, (9:1), 700 MHz, 298K] of Asp-Arg-Pro-Amb-Ile-His-Pro (Analogue 2) (SEQ ID NO: 2). *The C11H proton signals were not distinctly visible due to water suppression.
Figure 1C:
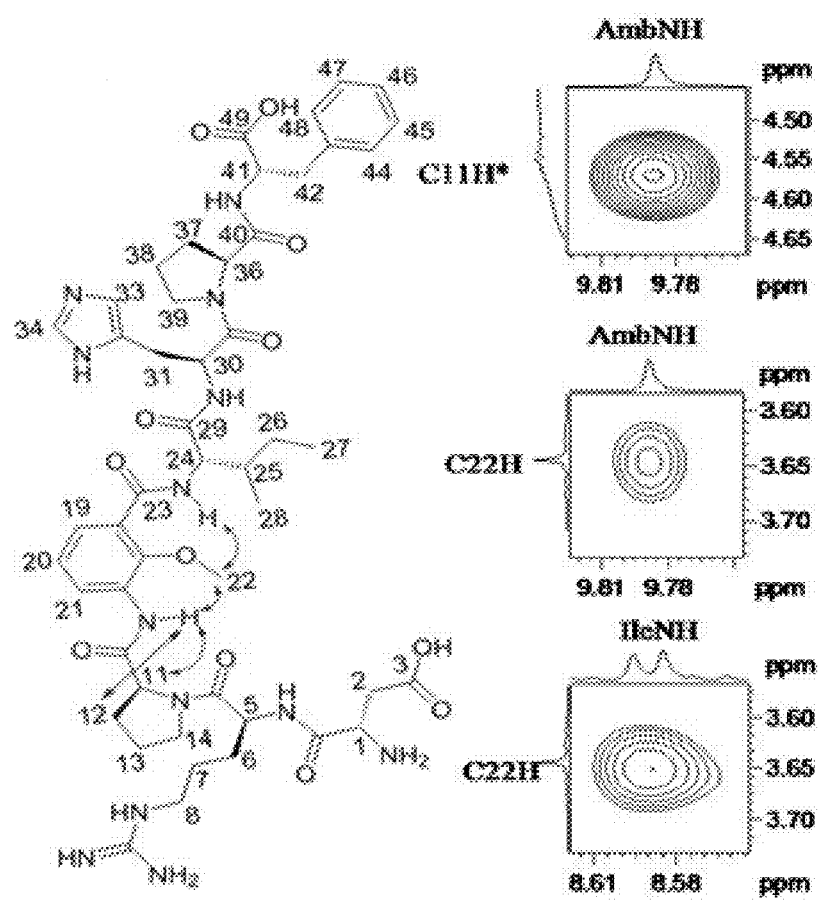
FIG. 1(c) represents the chemical structure and characteristic ROE excerpts for γ-turn conformation [$H_2O:D_2O$, (9:1), 700 MHz, 298K] of Asp-Arg-Pro-Amb-Ile-His-Pro-Phe (Analogue 1) (SEQ ID NO: 1). *The C11H proton signals were not distinctly visible due to water suppression.

Similar NOE interactions were observed between Amb-NH and α-hydrogen of proline in heptapeptide (Analogue 2) and octapeptide (Analogue 1), confirming the γ-turn in these peptides. Further, methyl from methoxy group of Amb showed NOE interactions with Amb-NH and IleuNH confirming extended 5- and 6-membered hydrogen bonds in Analogue 2 and Analogue 1, respectively (FIGS. 1(b) and (c)).

The observed NOEs under aqueous condition were in agreement with the earlier reported Pro-Amb oligomers in deuterated chloroform displaying γ-turn (i+2←i) stabilized by bifurcated hydrogen bonding (P. K. Baruah, et al, J. Org. Chem., 2007, 72, 636). It is described for the first time in the present invention through extensive solution state NMR and CD studies that the Pro-Amb adopts a stable γ-turn like conformation under aqueous conditions. None of the prior arts have reported hydrogen-bonding-restricted angiotensin II analogues with γ-turn like conformation stable under aqueous condition. From these findings, the stability of γ-turn-like secondary structure which is stabilized by bifurcated hydrogen bonding in analogues 1, 2 and 3 in aqueous solution was confirmed.

Figure 2:
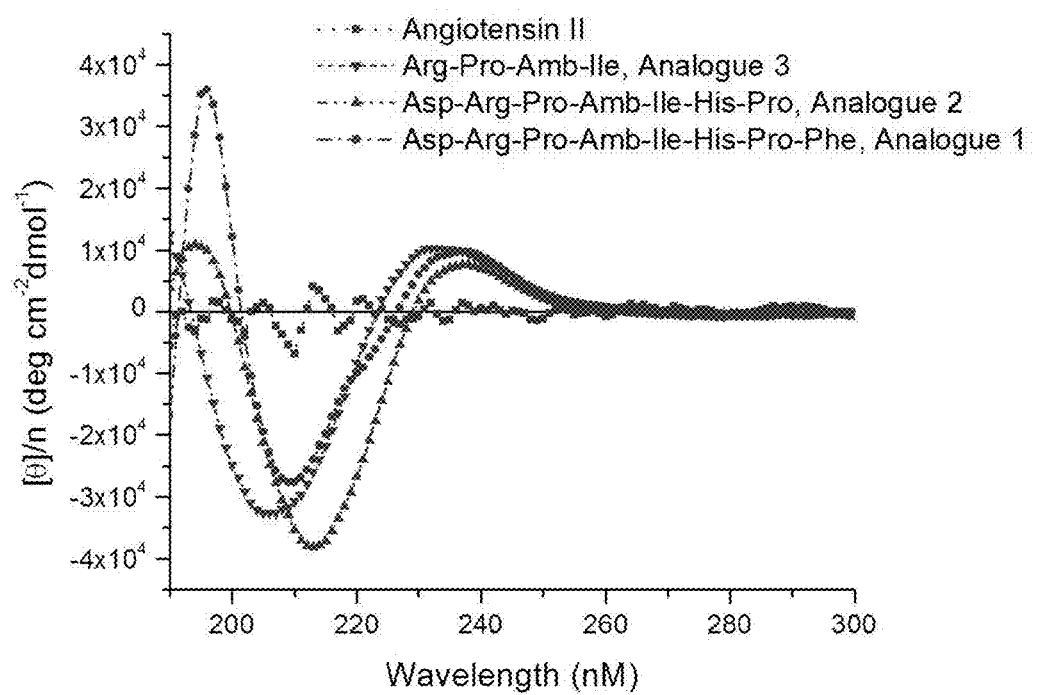
FIG. 2 depicts the circular dichroism spectra of Angiotensin II and SEQ ID NOs.1, 2 and 3 (0.2 mM in water)
Figure 3A:
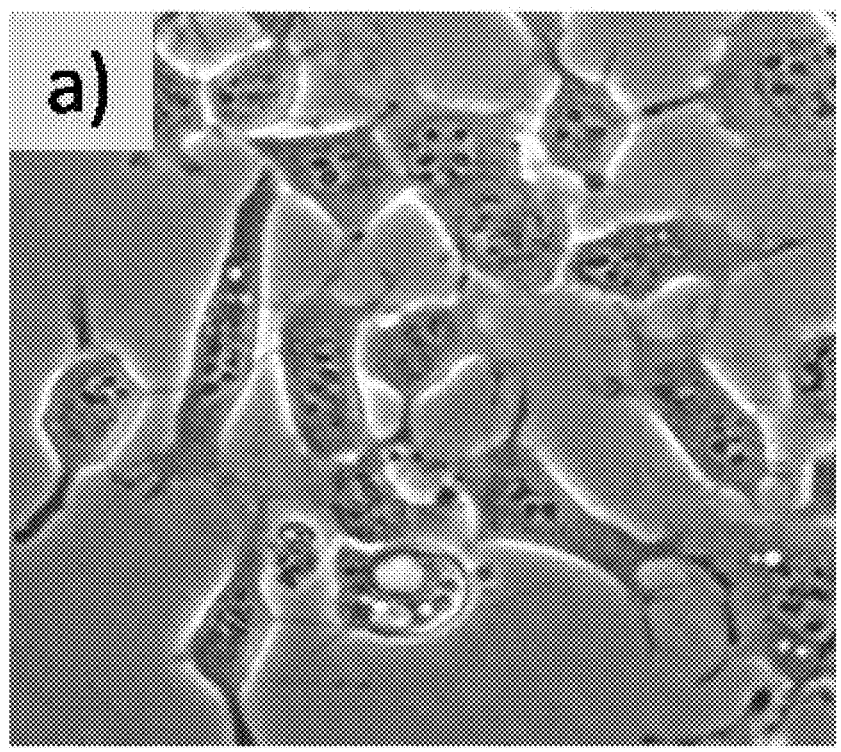
FIG. 3(a) depicts representative phase contrast images of NG108-15 cells displaying neurite outgrowth after 3 days treatment by control.
Figure 3B:
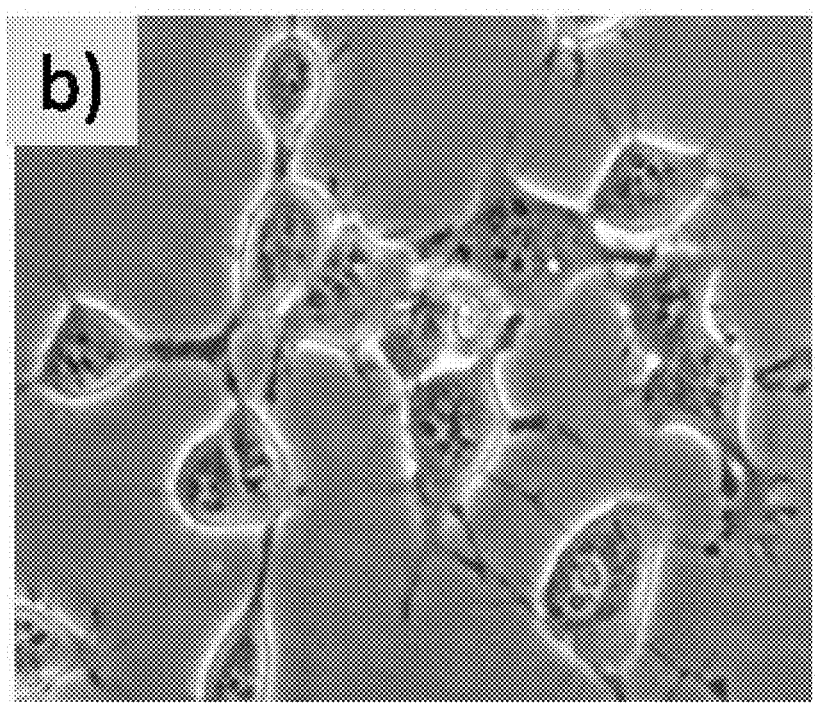
FIG. 3(b) depicts representative phase contrast images of NG108-15 cells displaying neurite outgrowth after 3 days treatment by PD 123319 (10 μM).
Figure 3C:
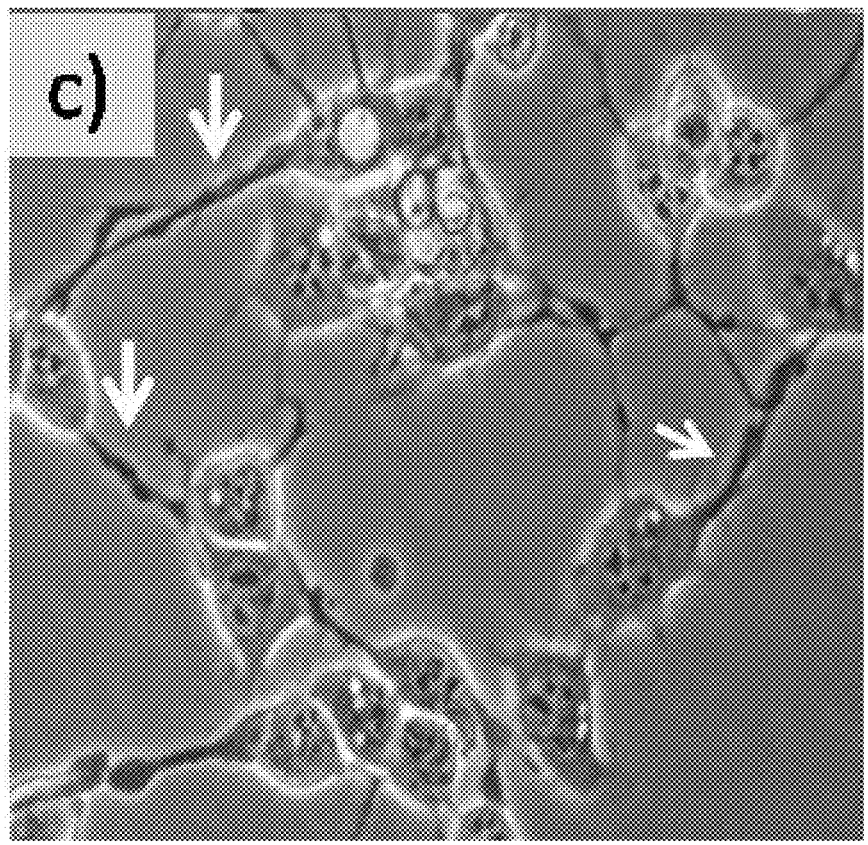
FIG. 3(c) depicts representative phase contrast images of NG108-15 cells displaying neurite outgrowth (highlighted by white arrows) after 3 days treatment by Ang II (100 nM).
Figure 3D:
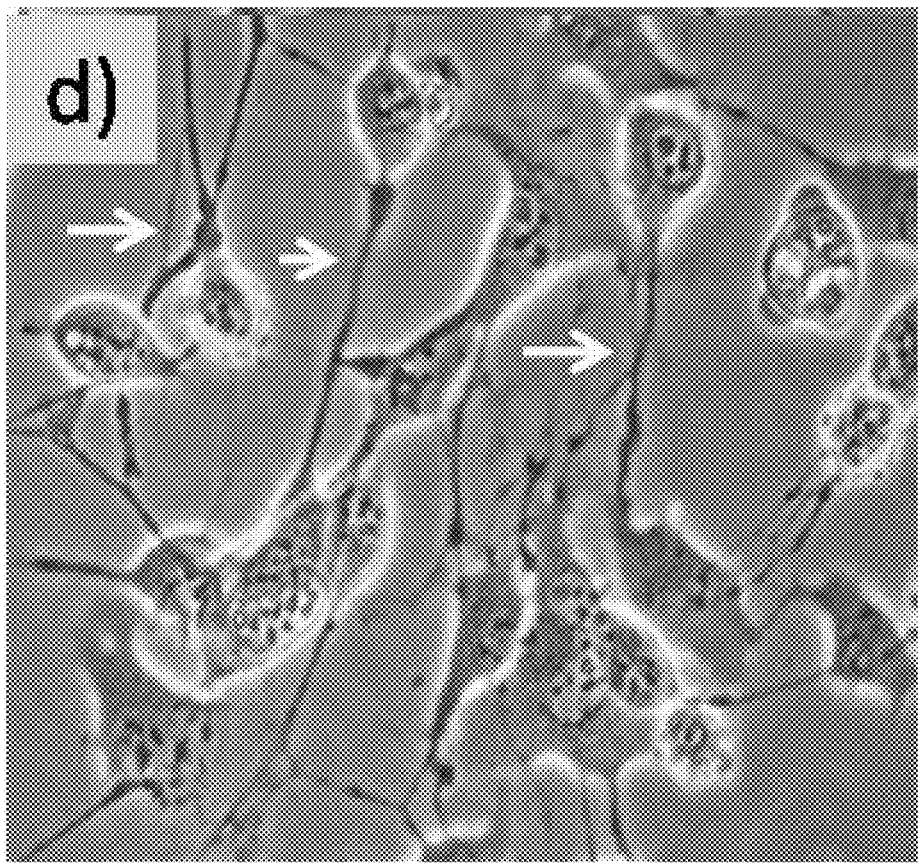
FIG. 3(d) depicts representative phase contrast images of NG108-15 cells displaying neurite outgrowth (highlighted by white arrows) after 3 days treatment by SEQ ID No.1 (1 μM). The cells in FIGS. 3(a)-3(d) were plated at an initial density of $3.6 \times 10^4$ cells/petri dish (35 mm).

Further, circular dichroism (CD) spectra of Pro-Amb analogues 2-3 in FIG. 2 indicated maxima around 195 nm and 235 nm and minima at 213 and 209 nm, respectively, in water. These finding suggests that peptides exist in turn-like conformation with content of β-sheet-like secondary structure in analogue 1. Analogue 2 has maxima at 235 nm followed by minima at 207 nm suggesting random coiled structure. These results are in agreement with 2D NMR data.

The chemical structures of the analogues are as follows:

Analogue 1

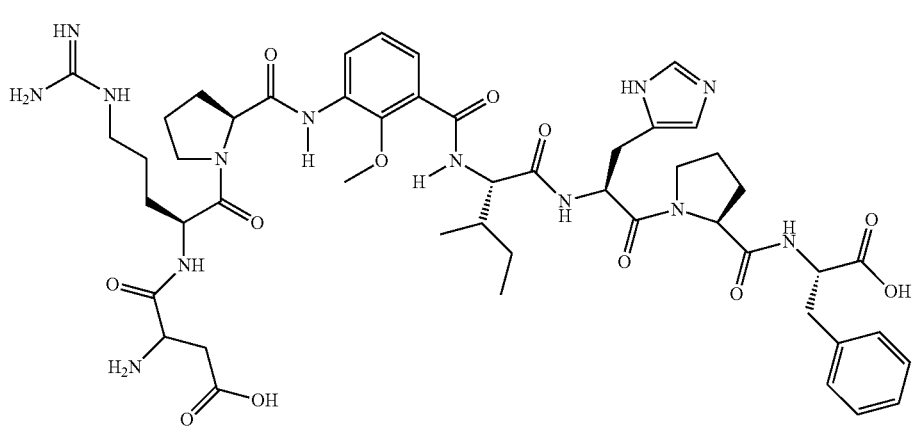

-continued

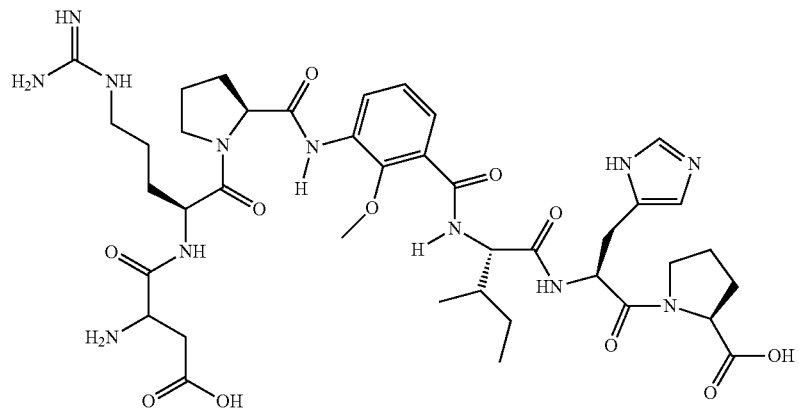

Analogue 2

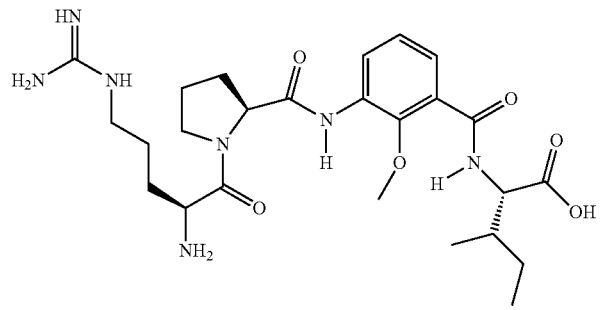

Analogue 3

In another embodiment of the present invention, the peptide or fragments thereof having Formula 1 are not cytotoxic upto concentrations ranging from 50 μM upto 150 μM.

Accordingly, the cytotoxicity of the analogues 1-3 were determined by MTT assay using HeLa cell lines (ATCC® CCL-2) and HepG2 (ATCC® HB-8065) cell lines at various concentrations and it was observed that these molecules were not cytotoxic upto 100 μM concentrations (data not shown).

Figure 4:
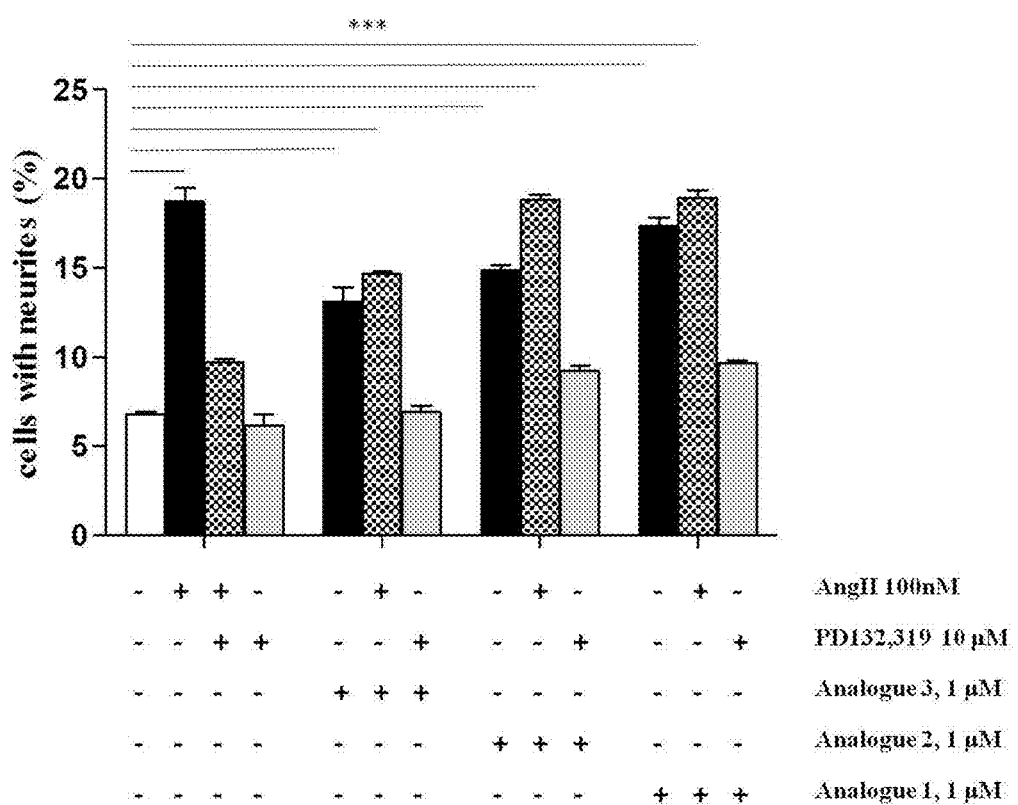
FIG. 4 depicts the quantification of neurite outgrowth experiment, the effect of analogues 3, 2 and 1 on neurite outgrowth in NG108-15 cells.

The functional activity of the analogues of the present invention was evaluated at the $AT_2$ receptor, applying a neurite outgrowth assay in NG108-15 [108CC15] (ATCC® HB12317™) cells. It was earlier reported by Blankley et al (J. Med. Chem., 1991, 34, 3248) that NG108-15 cells in their undifferentiated state express only the $AT_2$ receptor and that a 3-day treatment with Ang II or selective peptidic $AT_2$ receptor agonist CGP-42112A induces neurite outgrowth. The signaling pathways involve a sustained increase in Rap1/BRaf/p42/p44mapk activity and activation of the nitric oxide/guanylyl cyclase/cGMP pathway. NG108-15 cells were treated in absence or presence of Ang II and PD 123319, an $AT_2$ receptor antagonist. The cells were plated at the initial density of $3.6 \times 10^4$ cells/petri dish (35 mm) and were cultured for 3 days in the absence (−) or presence (+) of 100 nM Ang II, 1 μM analogue 3, analogue 2 and analogue 1 alone or in combination with 10 μM antagonist PD 123,319 or 100 nM AngII. After 3 days of treatment, the cells were examined under a phase contrast microscope and micrographs were taken. Cells with at least one neurite longer than a cell body were counted as a positive neurite outgrowth. Antagonistic effect was established through co-incubation with Ang II resulting in reduced Ang II-induced neurite outgrowth, verifying blockage of the $AT_2$ receptor. Agonistic effect was verified through co-incubation with selective $AT_2$ receptor antagonist PD 123319, which reduced neurite outgrowth, verifying that the effect was mediated through the $AT_2$ receptor (FIG. 4). The number of cells with neurites was expressed as the percentage of the total number in the micrographs (at least 260 cells according to the experiment). The results are significant according to two-way ANOVA whenever compared to control: ***, $p<0.001$. Treatment with PD 123319 alone did not alter the morphology compared to untreated cells. In case of Pro-Amb analogues 1, 2 and 3, there was enhancement in neurite outgrowth in NG108-15 cells when compared to control (FIG. 3. and FIG. 4). Further, there was no reduction in neurite outgrowth of Ang II when co-incubated with the analogues 1, 2 and 3 (FIG. 4). However, there was reduction in neurite outgrowth of analogues 1, 2, and 3 when co-incubated with PD123319 (10 μM). These observations confirm that analogues 1, 2 and 3 are acting as $AT_2$ receptor agonists and analogue 3 is preferably used in the present invention.

Ang II is not selective and is well known to bind and activate both the $AT_1$ and $AT_2$ receptors. However, analogues 1, 2 and 3 of the present invention, constrained into γ-turn-like conformation, may bind selectively to $AT_2$ receptor.

Yet another embodiment of the present invention provides a process for synthesis of the peptide or a fragment thereof having the Formula I by Fmoc-based solid-phase peptide synthesis using 2-chlorotritylchloride resin.

For the synthesis of Pro-Amb analogues 1, 2 and 3 of the present invention, 3-amino-2-methoxybenzoicacid (Amb) was Fmoc-protected using Fmoc-Cl in dioxane:water with sodium bicarbonate as a base and used further without purification. The Fmoc-Amb-OH was used for solid phase peptide synthesis, similar to other commercial Fmoc protected α-amino amino acids.

Purity of all peptide analogues was analysed by RP-HPLC using C-18 analytical column using 5% ACN to 90% ACN gradient in water and both the solvents containing 0.001% TFA and was estimated to be >90%.

Still another embodiment of the present invention provides a pharmaceutical composition comprising therapeutically effective amount of a peptide or a fragment thereof having the Formula I:

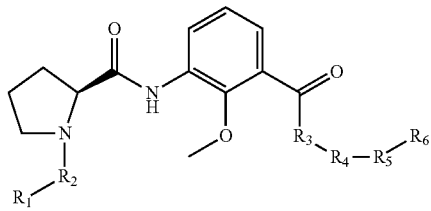

Formula I wherein $R_1$ is selected from the group consisting of aspartate (Asp), tyrosine (Tyr) and alanine (Ala), or $R_1$ is absent;

$R_2$ is selected from the group consisting of serine (Ser), arginine (Arg) and isoleucine (Ile);

$R_3$ is selected from the group consisting of tyrosine (Tyr), isoleucine (Ile) and serine (Ser);

$R_4$ is selected from the group consisting of tyrosine (Tyr), histidine (His) and glutamate (Glu), or $R_4$ is absent;

$R_5$ is selected from the group consisting of leucine (Leu), proline (Pro) and threonine (Thr), or $R_5$ is absent;

$R_6$ is selected from the group consisting of glutamate (Glu) and phenylalanine (Phe), or $R_6$ is absent, wherein proline-3-amino-2-methoxy benzoic acid (Pro-Amb) as a γ turn is incorporated between $R_2$ and $R_3$ and a pharmaceutically acceptable carrier.

In another embodiment of the present invention, there is provided a pharmaceutical composition comprising a peptide having SEQ ID NO: 1 (Asp-Arg-Pro-Amb-Ile-His-Pro-Phe) in a concentration of upto 150 μM.

The pharmaceutical composition of the present invention comprises pharmaceutically acceptable carriers selected from physiologically compatible buffers selected from the group consisting of physiological saline, i.e. Phosphate buffer saline (PBS), a mixture of saline and glucose, heparinized sodium-citrate-citric acid-dextrose solution, and other such acceptable carriers.

The pharmaceutical composition of the present invention can be administered intraperitoneally or intrathecally. The pharmaceutical composition of the present invention can be prepared in water mixed with a surfactant, such as hydroxypropylcellulose. Dispersions comprising said composition can also be prepared in glycerol and liquid polyethylene glycols or mixtures thereof. The composition can additionally comprise preservatives to prevent the growth of microorganisms when stored.

In case of sterile powders for preparation of sterile injectable solutions, methods of preparation of sterile powder include vacuum drying and freeze-drying techniques that yield a powder of the active ingredient plus any additional desired ingredient from a previously sterile-filtered solution thereof.

The route of administration of the pharmaceutical composition of the present invention is in accordance with procedure for protein therapeutic delivery to the central nervous system (CNS) described by conventional methods. The intracerebroventricular (ICV) route involves delivery of the pharmaceutical composition comprising the peptide of a fragment thereof having the formula I directly into the ventricle. ICV delivery is facilitated via an access port which is implanted in a pocket between the scalp and periosteum on top of the head, with a catheter placed directly into the ventricle. Further, intrathecal (IT) delivery is either performed by lumbar puncture or via port-catheter delivery systems. An implanted catheter is connected to an infusion pump, either implanted or external between the laminae of the lumbar vertebrae and the tip is threaded up the thecal space to the desired level.

Yet another embodiment of the present invention provides a method of treating a cognitive or a neurological disease comprising administration of a therapeutically effective concentration of a peptide or fragment thereof having the 1 formula I to a subject diagnosed with said cognitive or neurological disease or to a subject exhibiting symptoms of said cognitive or neurological disease.

Accordingly, the preferred peptide administered to a subject suffering from a cognitive disease is SEQ ID NO: 1.

For the purposes of the present invention, the cognitive diseases is described as those diseases associated with "a significant impairment of cognition or memory that represents a marked deterioration from a previous level of function" according to Guerrero, Anthony (2008) New York: Springer. pp. 367-79. The three main areas of cognitive disorders are delirium, dementia, Alzheimer's disease, and amnesia. Neurological disorders include dysfunctions of the central nervous system and the peripheral nervous system.

In another embodiment of the present invention, there is provided a method for treating a subject having a cognitive or a neurological diseases, said method comprising administering a therapeutically effective amount of a peptide or a fragments thereof having formula 1 selected from the group consisting of SEQ ID NO: 1, 2 and 3 or mixture thereof to a subject diagnosed with said disease or to a subject exhibiting symptoms of said disease followed by administering a Angiotensin II receptor ($AT_2R$) antagonist either simultaneously with the peptide or after a time interval.

The known $AT_2$ receptor antagonist is PD123319 while $AT_2$ receptor agonists are CGP42112A and C21. Further, the present invention also provides a combination product comprising a peptide or fragments thereof having Formula I and an $AT_2$ receptor agonist.

Administration of an $AT_2$ agonist along with an $AT_2$ receptor antagonist/$AT_1$ receptor antagonist either simultaneously or concomitantly after a time interval addresses the modulation of the renin-angiotensin system (RAS), related hypertension and diabetic nephropathy by means of said antagonist, as well as it provides beneficial protective effects of the AT2 agonist of the present invention.

In yet another embodiment of the present invention there is provided a use of the peptide or a fragment thereof having formula I for other therapeutic applications. The peptide or a fragment thereof having the formula I of the present invention can be further used in treatment of disorders of the central and peripheral nervous system, cardiovascular system, respiratory system gastro-intestinal tract, reproductive system, and renal system.

Cardiovascular diseases treated by the peptide having formula I of the present invention is characterised by hypertension, vasoconstriction, cardiomyopathy, cardiomegaly, ischemic lesions, thrombosis, increased cell growth and/or differentiation, increased cardiovascular hypertrophy, angiogenesis and several other related diseases. Respiratory diseases treated by the peptide having the formula I of the present invention include emphysema, extrinsic and intrinsic asthma, malignant pulmonary neoplasms, cell carcinoma of the lung and active sarcoidosis. Gastrointestinal diseases include inflammatory bowel disease, functional gut disorders, mucosal inflammation gastrointestinal malignancy and intestinal ischaemia.

Peptide or a fragment thereof having formula I of the present invention can also be used to regulate the process of growth metabolism and differentiation of cells in treatment of carcinomas, modulation of cell differentiation, tissue healing, neuronal lesions and in organ transplants.

EXAMPLES

Following examples are given by way of illustration therefore should not be construed to limit the scope of the invention.

Example 1: General Methods

2-Chlorotritylchloride resin and Fmoc protected amino acid derivatives were obtained from Novabiochem, Switzerland. DMF (lab reagent grade) was obtained from Merck and distilled twice over pthalic anhydride under reduced pressure. Dichloromethane-DCM (lab reagent grade) was obtained from Merck and distilled after overnight suspension over anhydrous $K_2CO_3$ (Merck). 3-Amino-2-methoxy-benzoic acid, N,N'-diisopropylcarbodiimide (DIC) and dicyclohexylcarbodiimide (DCC) were obtained from Sigma-Aldrich. 1-hydroxybenzotriazole (HOBt) was purchased from Anaspec. All other reagents were obtained from commercial sources and were used as received. The purity of synthesized peptides was analyzed using analytical RP-HPLC as described in example 2 (SPPS section). The characterization of synthesized peptides was performed using circular dichroism (CD), fourier transform infrared spectroscopy (FTIR), nuclear magnetic resonance (NMR), high resolution mass-spectroscopy (HRMS), etc. The NMR studies were performed on 700 MHz Bruker instrument using $H_2O:D_2O$ (9:1) as a solvent. In the $^1H$ NMR spectra, it was not possible to integrate the peaks due to water suppression; hence the number of protons in NMR peak was assigned using HSQC (heteronuclear single quantum coherence spectroscopy) and HMBC (heteronuclear multiple bond correlation).

Example 2: Solid-Phase Peptide Synthesis (SPPS)

Designed peptides were synthesized using solid phase peptide synthesis (SPPS) on semi-automatic peptide synthesizer act-90 from Advanced Chemtec using Fmoc/tert-butyl protection. The starting polymer was 2-chlorotritylchloride resin (1.6 mmol/g) and for the Fmoc amino acids, the side chain protecting groups were Asp(OtBu), Arg(Pbf) and His(Trt). Removal of the F-moc group was achieved by reaction with 20% piperidine in DMF for 10 min thrice. Coupling of the amino acids (4 equiv.) were performed in DCM:DMF (1:1) (10 ml) using DIC:HOBt (1:1) (4 equiv.) for 90 min Completion of coupling was confirmed by positive and negative Kaiser test.

For proline (Pro) and 3-amino-2methoxy-benzoic acid (Amb), isatin and chloranil tests were used, respectively. After the introduction of each amino acid, excess amino acids were washed by DMF, four times. The final peptide resins were cleaved by a cleavage cocktail:TFA/$H_2O$/TIS/EDT/phenol (250:2.5:1:1:1), for 4 h. The filtrate was concentrated on rota-vapour at reduced pressure and later co-evaporated with distilled diethyl ether, twice. The residue obtained was dissolved in minimum volume of methanol and desalted by eluting through sephadex LH-20 chromatography using methanol as mobile phase. The desired fractions were confirmed by LCMS and lyophilized to obtain peptide as a white amorphous powder. The purity of the peptides was examined by analytical RP-HPLC using LiChrosolv C-18 column with a flow-rate of 0.8 ml/min and the pressure was 1400 psi. The mobile phases for HPLC were 0.001% TFA in ACN (solvent A) and 0.001% TFA in $H_2O$ (solvent B). The gradients of solvent A to solvent B were varied as follows: 0 to 5 min (10%), 5 to 40 min (10% to 90%), 40 to 45 min (90% to 10%) and 45 to 50 min (10%).

Example 3: Synthesis of 3-((((9H-fluoren-9-yl)methoxy)carbonyl)amino)-2-methoxybenzoicacid 3-Amino-2-methoxybenzoic acid (1 equiv.) was dissolved in dioxane (2:1) and an aqueous solution of sodium bicarbonate (2 eq) was added with stirring. The resulting solution was cooled to 5° C. and Fmoc-Cl (1.05 eq) was added slowly as a solution in dioxane (cooled). The resulting mixture was stirred at 0° C. for 1 h and allowed to warm to room temperature overnight. Dioxane was evaporated on rota vapour. The concentrate was precipitated using 2N HCl. Then, it was filtered and the residue was washed several times with water. The off-white powder obtained from residue was air dried for two days and used further on SPPS without any further purification.

2-(3-{[1-(2-Amino-5-guanidino-pentanoyl)-pyrrolidine-2-carbonyl]-amino}-2-methoxy-benzoylamino)-3-methyl-pentanoic acid The peptide having SEQ ID NO: 3 (analogue 3) was prepared as mentioned in example 2 of SPPS. $[\alpha]^{25.3}_D$: 4.1 (c 0.002, $CH_3OH$). IR (nujol) $\nu$ ($cm^{-1}$): 3376.96, 3087.66, 3062.93, 3027.69, 2925, 2856.17, 2729.31, 1854.86, 1700.76, 1652.98, 1605.34, 1496.08, 1489.41, 1461.52, 1377.61, 1312.3, 1209.32, 1155.41, 1081.56, 1030.54, 893.73, 843.5, 727.8, 694.26. $^1H$ NMR[1] (700 MHz, $H_2O$:$D_2O$ (9:1)) δ: 9.84 (s, 1H), 8.70 (d, J=7.9 Hz, 1H), 8.07 (broad, 1H), 7.61 (dd, J=8.11, 1.5 Hz, 1H), 7.44 (dd, J=7.9, 1.4 Hz, 1H), 7.20 (t, J=7.9 Hz, 1H), 7.09 (t, J=5.9 Hz, 1H), 6.55 (broad, 1H), 4.65 (m, 1H), 4.41 (m, 1H), 4.36 (t, J=6.1×(2)Hz, 1H), 3.75-3.69 (m, 5H), 3.60-3.57 (m, 2H), 3.15-3.12 (m, 2H), 2.41-2.37 (m, 1H), 2.08-1.88 (m, 5H), 1.68-1.57 (m, 2H), 1.48-1.43 (m, 1H), 1.24-1.19 (m, 1H), 0.93 (d, J=6.9 Hz, 3H), 0.84 (t, J=7.5 Hz, 3H). $^{13}C$ NMR (176 MHz, $H_2O$:$D_2O$ (9:1)) δ: 176.9, 174.2, 170.0, 169.4, 158.2, 158.1, 152.2, 130.9, 130.3, 129.2, 128.7, 126.0, 63.5, 62.2, 59.7, 59.6, 52.7, 49.3, 41.7, 41.6, 37.7, 30.6, 28.2, 26.0, 26.0, 24.2, 16.3, 11.8. HRMS $C_{25}H_{40}O_3N_7$ $[M+H]^+$ calculated mass 534.3035, observed mass 534.3026.

1-[2-{2-[3-({1-[2-(2-Amino-3-carboxy-propionylamino)-5-guanidino-pentanoyl]-pyrrolidine-2-carbonyl}-amino)-2-methoxy-benzoylamino]-3-methyl-pentanoylamino}-3-(1H-imidazol-4-yl)-propionyl]-pyrrolidine-2-carboxylic acid The peptide having SEQ ID NO: 2 (analogue 2) was prepared as mentioned in example 2 of SPPS. $[\alpha]^{25.42}_D$: −32.9067 (c 0.003, $CH_3OH$). IR (nujol) $\nu$ ($cm^{-1}$): 3554.11, 3365.11, 3171.62, 3087.11, 2919.62, 2727.52, 2670.93, 2036.48, 1937.58, 1855.22, 1702.99, 1605.47, 1496.2, 1461.21, 1377.55, 1307.96, 1204.93, 1170.55, 1154.55, 1081.3, 1042.46, 1030.52, 973.78, 893.1, 842.74, 800.69, 727.72, 694.26, 666.04, 594.63. $^1H$ NMR[1] (700 MHz, $H_2O$:

$D_2O$ (9:1)) δ: 9.79 (s, 1H), 8.65-8.61 (m, 5H), 8.50 (d, J=1.3 Hz, 1H), 7.6 (dd, J=8.1, 1.4 Hz, 1H), 7.37 (dd, J=7.8, 1.5 Hz, 1H), 7.26 (s, 1H), 7.2 (t, J=7.9×(2) Hz, 2H), 7.08 (t, J=5.5×(2) Hz, 2H), 5.98 (m, 1H), 4.64 (m, 1H), 4.57 (m, 1H), 4.31 (m, 1H), 4.27 (m, 2H), 3.8 (m, 2H), 3.71 (m, 2H), 3.65 (s, 3H), 3.62 (m, 2H), 3.53 (m, 2H), 3.19 (m, 1H), 3.1 (m, 3H), 2.93 (dd, J=17.9, 4.7 Hz, 1H), 2.83 (dd, J=17.9, 8.1 Hz, 1H), 2.35 (m, 1H), 2.21 (m, 1H), 2.02 (m, 3H), 1.91 (m, 3H), 1.78 (m, 2H), 1.68 (m, 1H), 1.61 (m, 2H), 1.4 (m, 1H), 1.15 (m, 1H), 0.82 (m, 3H), 0.79 (m, 3H). $^{13}C$ NMR (176 MHz, $H_2O+D_2O$) δ=177.7, 174.7, 174.6, 174.6, 174.4, 172.5, 170.6, 169.9, 169.9, 158.1, 158.1, 152.1, 134.8, 134.8, 131.0, 130.5, 129.4, 129.0, 128.6, 126.1, 118.9, 63.4, 62.2, 61.4, 60.0, 52.8, 52.7, 51.5, 51.0, 49.3, 49.0, 48.2, 41.9, 37.4, 36.7, 32.2, 30.7, 30.2, 28.7, 27.1, 26.0, 25.8, 25.7, 25.2, 16.0, 11.2. HRMS $C_{40}H_{59}O_{11}N_{12}$ [M+H]$^+$ calculated mass 883.4421, observed mass 883.4428; $C_{40}H_{58}O_{11}N_{12}Na$ [M+Na]$^+$ calculated mass 905.4240, observed mass 905.4240.

3-Amino-N-{1-[2-(3-{1-[2-[2-(1-carboxy-2-phenyl-ethylcarbamoyl)-pyrrolidin-1-yl]-1-(1H-imidazol-4-ylmethyl)-2-oxo-ethylcarbamoyl]-2-methyl-butylcarbamoyl}-2-methoxy-phenylcarbamoyl)-pyrrolidine-1-carbonyl]-4-guanidino-butyl}-succinamic acid The peptide having SEQ ID NO: 1 (analogue 1) was prepared as mentioned in example 2 of SPPS. $[α]^{25.3}_D$: −21.2 (c 0.002, $CH_3OH$). IR (nujol) ν ($cm^{-1}$): 3365.62, 3177.77, 2922.83, 2854.97, 2725.92, 2363.75, 2041.28, 1700.75, 1653.17, 1461.22, 1377.47, 1310.21, 1204.97, 1155.51, 1080.39, 973.4, 892.96, 847.48, 801.42, 727.55, 694.17, 667.8, 552.2, 540.09. $^1H$ NMR$^1$ (700 MHz, $H_2O$: $D_2O$ (9:1)) δ: 9.79 (s, 1H), 8.64 (d, J=7.52 Hz, 1H), 8.59 (d, J=7.5 Hz, 1H), 8.54 (d, J=8.11 Hz, 1H), 8.47 (m, 1H), 8.18 (d, J=7.52 Hz, 1H), 7.61 (m, 1H), 7.37 (m, 1H), 7.27 (m, 2H), 7.2 (m, 4H), 7.08 (t, J=5.88 Hz, 1H), 6.57 (broad, 1H), 4.98 (m, 1H), 4.63 (m, 1H), 4.56 (m, 1H), 4.54 (m, 1H), 3.8 (m, 2H), 3.65 (m, 3H), 3.52 (m, 1H), 3.11 (m, 4H), 3.02 (m, 2H), 2.94 (m, 1H), 2.83 (m, 1H), 2.35 (m, 1H), 2.12 (m, 1H), 2.0 (m, 3H), 1.86 (m, 2H), 1.78 (m, 3H), 1.68 (m, 1H), 1.6 (m, 2H), 1.38 (m, 1H), 1.14 (m, 1H), 0.79 (m, 6H). $^{13}C$ NMR (176 MHz, $H_2O:D_2O$(9:1)) δ: 176.4, 174.9, 174.7, 174.6, 174.4, 172.5, 170.8, 170.0, 169.9, 158.2, 158.1, 152.2, 137.8, 134.8, 131.0, 130.5, 129.9, 129.5, 129.0, 128.6, 128.3, 126.1, 118.9, 63.4, 62.2, 61.7, 60.1, 55.8, 52.8, 52.7, 51.5, 51.1, 49.3, 49.2, 41.9, 37.8, 37.4, 36.8, 30.7, 30.5, 28.7, 27.2, 26.0, 25.8, 25.7, 25.2, 16.0, 11.2. HRMS $C_{49}H_{68}O_{12}N_{13}$ [M+H]$^+$ calculated mass 1030.5105, observed mass 1030.5105; $C_{49}H_{67}O_{12}N_{13}Na$ [M+Na]$^+$ calculated mass 1052.4924, observed mass 1052.4916.

Example 4: Cell Culture. To Study In Vitro Morphological Effects ($AT_2$ Receptor Agonistic/Antagonistic Activity)

NG108-15 [108CC15] (ATCC® HB12317™) cells were cultured in Dulbecco's modified Eagle's medium with 10% fetal bovine serum, HAT supplement (hypoxanthine, aminopterin and thymidine), and 50 mg/L gentamycin at 37° C. in 75 $cm^2$ Nunclon Delta flasks in a humidified atmosphere of 95% air and 5% $CO_2$. Subcultures were performed at sub-confluency. Under these conditions, cells express only the $AT_2$ receptor subtype (Payet, *FEBS Lett.*, 1992, 309, 161). Cells were stimulated during 3 days (once daily)—(first stimulation 24 h after plating). Cells were cultured for 3 subsequent days under these conditions. For all experiments, cells were plated at the same initial density of 3.6×10$^4$ cells/35 mm Petri dish and test concentrations for compounds used were 1 μM and 0.1 μM. Cells were then treated in the absence or presence of Ang II (100 nM), PD 123,319 (10 μM) $AT_2$ receptor antagonist. After 3 days of treatment, cells were examined under a phase contrast microscope and micrographs were taken. For determination of cells with Neurites, cells were examined under a phase contrast microscope, and micrographs were taken after 3 days under various experimental conditions. Cells with at least one neurite longer than a cell body were counted as positive for neurite outgrowth. The number of cells with neurites represents the percentage of the total amount of cells in the micrographs. At least two different experiments were conducted for each condition, each in duplicate. At least five images were taken per petri dish; hence, a total of 250-400 cells from each of the duplicate dishes were examined.

Advantages of the Present Invention

Stimulation of the $AT_2$ receptor ($AT_2R$) by an $AT_2$ receptor agonist prevents neural damage and cognitive impairment. The present invention provides a peptide or a fragment thereof having formula I which acts as an $AT_2$ receptor agonist which can be used for treatment neurological disorders and other cognitive dysfunctions.

$AT_2R$ stimulation by the peptide or a fragment thereof having formula I of the present invention can be exploited in treatment of hypertension, renal disease, stroke, Alzheimer's disease, myocardial infarction and in tissue protection in diseased conditions.

Insertion of Pro-Amb scaffold in a bioactive peptide to mimic a turn like conformation in the secondary structure of a protein helps in designing analogues for different therapeutic proteins, thereby enhancing receptor or ligand binding affinity.

We claim:

1. A peptide or a fragment thereof having the Formula I:

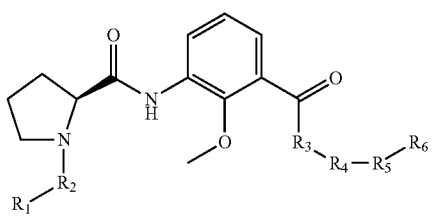

Formula I wherein $R_1$ is selected from the group consisting of aspartate (Asp), tyrosine (Tyr) and alanine (Ala), or $R_1$ is absent;

$R_2$ is arginine (Arg);

$R_3$ is isoleucine (Ile);

$R_4$ is selected from the group consisting of tyrosine (Tyr), histidine (His) and glutamate (Glu), or $R_4$ is absent;

$R_5$ is selected from the group consisting of leucine (Leu), proline (Pro) and threonine (Thr), or $R_5$ is absent;

$R_6$ is selected from the group consisting of glutamate (Glu) and phenylalanine (Phe), or $R_6$ is absent, wherein proline-3-amino-2-methoxy-2-benzoic acid (Pro-Amb) has a γ-turn configuration between $R_2$ and $R_3$.

2. The peptide according to claim 1, wherein a γ-turn configuration is between 3-amino-2-methoxy benzoic acid (Amb) and $R_2$ through hydrogen bonding which is stable under aqueous conditions.

3. The peptide according to claim 1, wherein the peptide of formula I is analogue 1

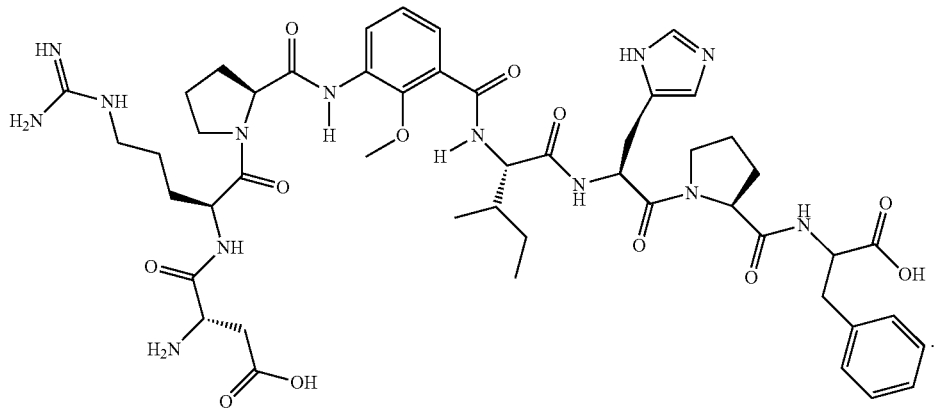

Analogue 1

4. The peptide according to claim 1, wherein the peptide of formula I is analogue 2

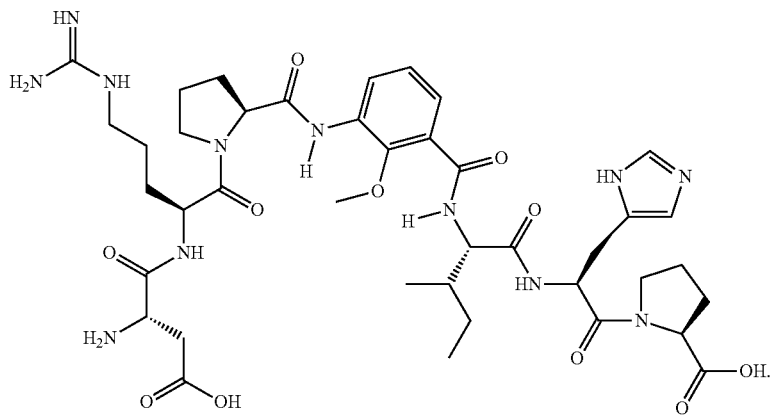

Analogue 2

5. The peptide according to claim 1, wherein the peptide of formula I is analogue 3

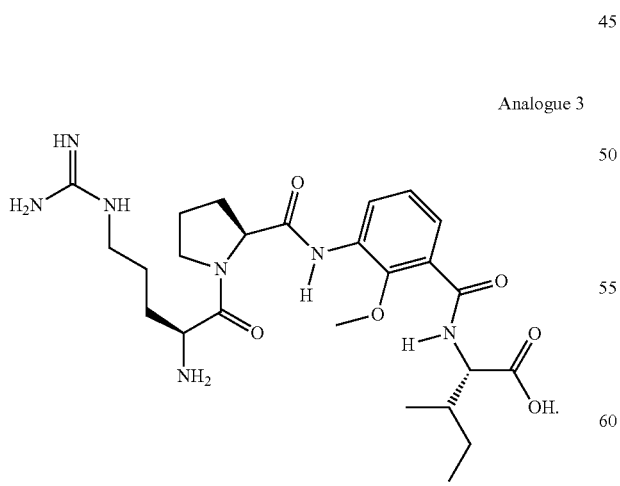

Analogue 3

6. A pharmaceutical composition comprising a peptide or a fragment thereof having the Formula 1:

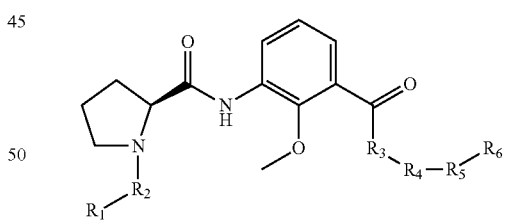

Formula I wherein $R_1$ is selected from the group consisting of aspartate (Asp), tyrosine (Tyr) and alanine (Ala), or $R_1$ is absent;
$R_2$ is arginine (Arg);
$R_3$ is isoleucine (Ile);
$R_4$ is selected from the group consisting of tyrosine (Tyr), histidine (His) and glutamate (Glu), or $R_4$ is absent;
$R_5$ is selected from the group consisting of leucine (Leu), proline (Pro) and threonine (Thr), or $R_5$ is absent;
$R_6$ is selected from the group consisting of glutamate (Glu) and phenylalanine (Phe), or $R_6$ is absent,
wherein proline-3-amino-2-methoxy-2-benzoic acid (Pro-Amb) has a γ-turn configuration between $R_2$ and $R_3$;
and a pharmaceutically acceptable carrier.

7. The pharmaceutical composition according to claim 6, wherein the pharmaceutically acceptable carrier is a physiologically compatible buffer selected from the group consisting of:
Phosphate buffer saline (PBS),
a mixture of saline and glucose, and
heparinized sodium-citrate-citric acid-dextrose solution.

* * * * *